United States Patent [19]

Sandvig et al.

[11] Patent Number: 5,800,899
[45] Date of Patent: Sep. 1, 1998

[54] ORTHOPEDIC CASTING MATERIAL HAVING IMPROVED WET STRENGTH

[75] Inventors: Timothy C. Sandvig, Woodville, Wis.; Dean A. Ersfeld, Maplewood, Minn.; Daniel W. Davis, Hugo, Minn.; Steven H. Gotz, Woodbury, Minn.

[73] Assignee: Minnesota Mining and Manufacturing Company, St. Paul, Minn.

[21] Appl. No.: 462,838

[22] Filed: Jun. 5, 1995

[51] Int. Cl.⁶ .................................................. A61F 5/00
[52] U.S. Cl. .................... 428/96; 428/92; 442/1; 442/180; 442/304; 602/8
[58] Field of Search .................. 428/92, 96, 228; 602/8; 442/1, 180, 304

[56] References Cited

U.S. PATENT DOCUMENTS

| | | |
|---|---|---|
| 3,686,725 | 8/1972 | Nisbet et al. . |
| 3,908,644 | 9/1975 | Neinart et al. . |
| 4,411,262 | 10/1983 | von Bonin et al. . |
| 4,433,680 | 2/1984 | Yoon . |
| 4,502,479 | 3/1985 | Garwood et al. . |
| 4,609,578 | 9/1986 | Reed . |
| 4,667,661 | 5/1987 | Scholz et al. . |
| 4,668,563 | 5/1987 | Buese et al. ............ 428/230 |
| 4,705,840 | 11/1987 | Buckanin ............ 528/53 |
| 4,841,958 | 6/1989 | Ersfeld et al. . |
| 4,940,047 | 7/1990 | Richter et al. . |
| 4,984,566 | 1/1991 | Sekine et al. . |
| 5,014,403 | 5/1991 | Buese . |
| 5,206,064 | 4/1993 | Scholz ............ 428/86 |
| 5,244,997 | 9/1993 | Scholz et al. ............ 602/6 |
| 5,273,802 | 12/1993 | Scholz et al. ............ 428/76 |
| 5,353,486 | 10/1994 | Schmidt et al. . |
| 5,354,259 | 10/1994 | Scholz et al. ............ 602/8 |

FOREIGN PATENT DOCUMENTS

| | | |
|---|---|---|
| 0 407 056 | 1/1991 | European Pat. Off. . |
| 2 279 356 | 1/1995 | United Kingdom . |
| WO 95/19751 | 7/1995 | WIPO . |

OTHER PUBLICATIONS

PCT Written Opinion for PCT/US96/05857 (USSN 08/462,838).

Temple C. Patton, "Review of Fundamentals and Advances In Urethane Coating Technology", *Journal of Paint Technology*, vol. 39, No. 512, Sep. 1967, pp. 554–563.

Bernard A. Dombrow, *Polyurethanes*, Second Edition, Reinhold Publishing Corporation, New York, pp. 78–81 and pp. 204–205.

PCT Search Report for PCT/US96/05857 (USSN 08/462,838).

*Primary Examiner*—James J. Bell
*Attorney, Agent, or Firm*—F. Andrew Ubel

[57] ABSTRACT

An orthopedic casting material is disclosed comprising a water-curable, isocyanate-functional prepolymer. The prepolymer comprises the reaction product of a polyisocyanate and a polyol having an HLB number per hydroxy group less than zero.

28 Claims, 1 Drawing Sheet

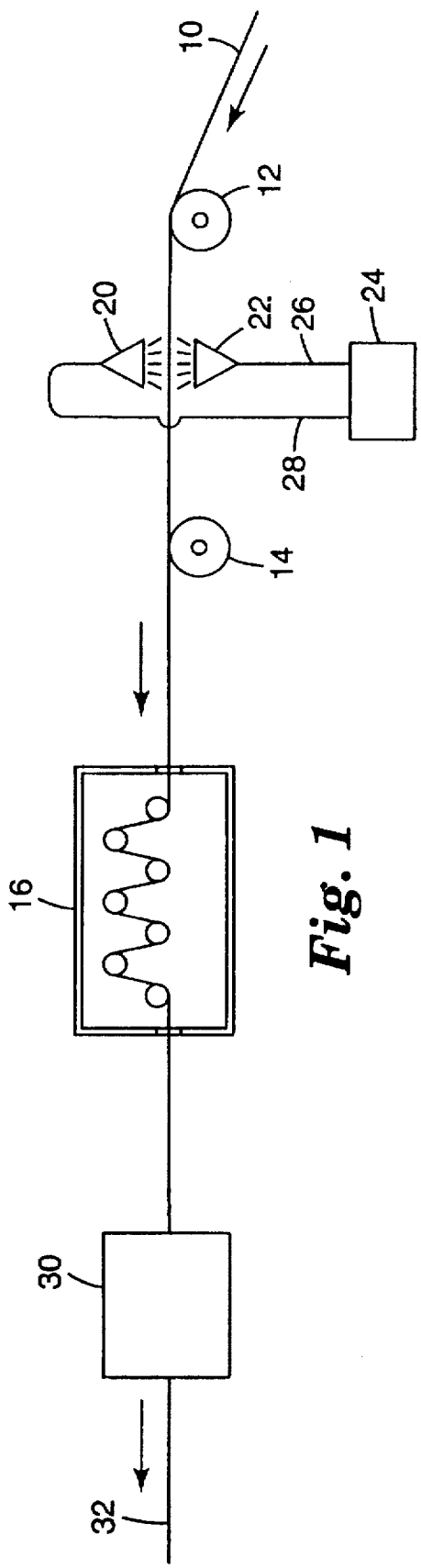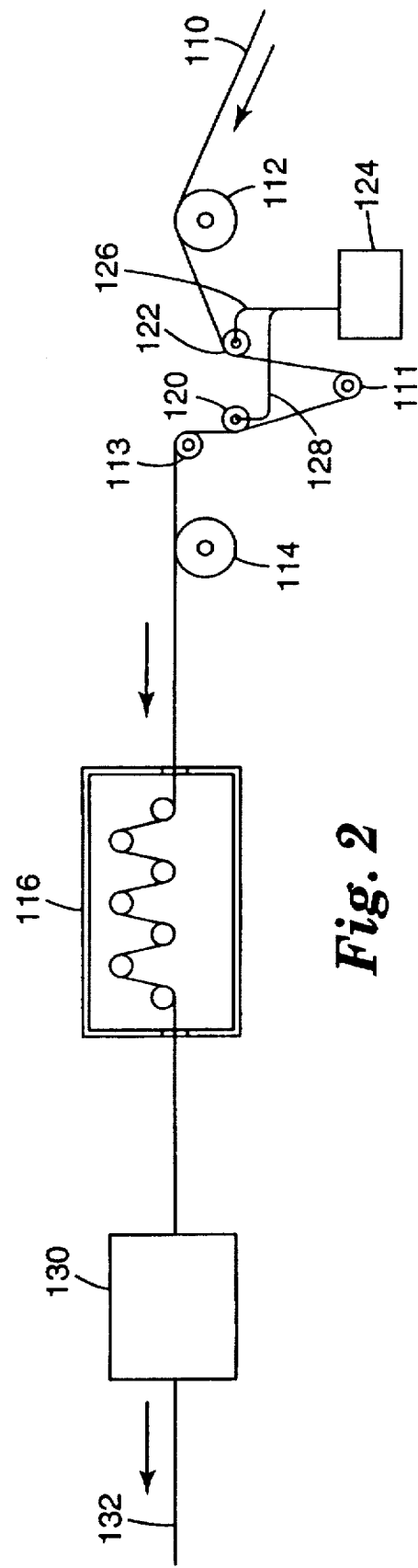

5,800,899

1

ORTHOPEDIC CASTING MATERIAL HAVING IMPROVED WET STRENGTH

FIELD

This invention relates to orthopedic casting materials.

BACKGROUND

Many different orthopedic casting materials have been developed for use in the immobilization of broken or otherwise injured body limbs. Some of the first casting materials developed for this purpose involved the use of plaster of Paris bandages consisting of a mesh fabric (e.g., cotton gauze) with plaster incorporated into the openings and onto the surface of the mesh fabric. Subsequently, improved casting materials were developed consisting of a knit fabric made from a high modulus fiber (e.g., fiberglass) impregnated with a polyisocyanate prepolymer. The prepolymer typically was the reaction product of a polyisocyanate and a hydrophilic polyol such as a polyether- or polyester-based polyol. One problem with such materials, however, was that their strength decreased significantly once they got wet.

SUMMARY

In a first aspect, the present invention features an orthopedic casting material that includes a porous fabric provided with a water-curable, isocyanate-functional prepolymer that includes the reaction product of a polyisocyanate and a polyol having an HLB number per hydroxy group less than zero. Using hydrophobic polyols having HLB numbers less than zero improves the warm wet strength of the material following cure.

In preferred embodiments, the prepolymer is a coatable prepolymer. The polyol preferably has an HLB number per hydroxy group less than −3, and, more preferably, less than −5. Examples of preferred polyols include hydroxylated fatty acids (or esters thereof), e.g., glyceryl polyhydroxyoleates such as glyceryl trihydroxyoleates. A particularly preferred polyol is castor oil. Preferably, the warm wet strength of the material following cure is at least 35N/cm, as measured according to the test procedure described infra. More preferably, the warm wet strength is at least 40N/cm, most preferably the warm wet strength is at least 60N/cm, and optimally the warm wet strength is at least 90N/cm.

The porous fabric preferably includes a knitted or woven fabric such as fiberglass fabric. The fabric may be provided with one or more lubricants and/or silane coupling agents as well. In one embodiment, the fabric is a knitted or woven fiberglass fabric having on at least one side thereof a plurality of projections, each of which includes a bundle of at least about 8 filaments. Preferably, there are about 75 to about 1500 projections per gram of fabric, and, more preferably, about 1 to about 50 projections per gram of fabric. In another embodiment, the fabric includes a lightweight scrim, in which case the casting material further includes one or more fillers in an amount such that the total volume of the fillers divided by the volume of prepolymer is greater than about 0.4.

Other ingredients which may be added to the casting material include one or more microfiber fillers having an aspect ratio of at least 5:1, and antifoaming agents.

In a second aspect, the invention features an orthopedic casting material that includes (a) one or more fillers; and (b) a water-curable, isocyanate-functional prepolymer that includes the reaction product of a polyisocyanate and a polyol having an HLB number per hydroxy group less than

2 zero. The orthopedic casting material has a sufficient void volume such that (a) prior to cure the material has sufficient tensile strength to resist tensile stresses imparted during wrapping of a cast and (b) upon cure the material has sufficient porosity to allow transport of water vapor.

In a third aspect, the invention features a method of applying an orthopedic casting material that includes the steps of (1) contacting an orthopedic casting material with water to initiate cure of the casting material, (2) applying the casting material to a patient, and (3) causing the casting material to harden. The casting material includes a porous fabric provided with a water-curable, isocyanate-functional prepolymer that includes the reaction product of a polyisocyanate and a polyol having an HLB number per hydroxy group less than zero.

In a fourth aspect, the invention features a continuous process for applying silanes to the surface of a porous fabric web (e.g., a fiberglass fabric web) that includes the steps of:

introducing a porous fabric in the form of a continuously moving web into a silane application zone;

applying a solution that includes one or more silanes to the surface of the web in the silane application zone;

introducing the web into a drying zone located downstream of the silane application zone following application of the solution;

drying the surface of the web in the drying zone;

coating the web with a curable resin in a coating zone located downstream of the drying zone; and converting (e.g., cutting and/or rolling) the resin coated web into individual rolls of casting tape.

In preferred embodiments, the solution may be applied to the web by atomizing the solution to form an atomized spray and spraying atomized spray onto the surface of the web in the silane application zone. Another way of applying the solution to the web is by providing a porous pipe containing the solution, and then causing the solution to flow through the pores of the pipe onto the surface of the web in the silane application zone.

By using a prepolymer prepared using a hydrophobic polyol (i.e., a polyol having an HLB number per hydroxy group less than zero), the invention provides orthopedic casting materials having improved wet strength relative to casting materials prepared using more hydrophilic polyols such as polyester- and polyether-based polyols. In many cases, the prepolymer can be prepared from readily available and inexpensive polyols such as castor oil.

The warm wet strength of the article may be further improved by providing the surface of the porous fabric with a silane coating. The invention provides a continuous process for applying such a coating to a bundle of the porous fabric that minimizes the amount of silane needed (and thus overall cost).

Other features and advantages of the invention will be apparent from the following description of preferred embodiments thereof, and from the claims.

BRIEF DESCRIPTION OF THE DRAWINGS

FIG. 1 is a schematic representation of one method of applying a silane coupling agent to the surface of a porous fabric sheet in which the coupling agent is applied in the form of an atomized spray.

FIG. 2 is a schematic representation of a second method of applying a silane coupling agent to the surface of a porous fabric sheet in which the coupling agent is applied by means of a porous pipe.

DEFINITIONS

Throughout this application, the following definitions apply:

"HLB number" refers to the hydrophilic-lipophilic balance number according to the Atlas ELB system for rating surfactants (which balances off hydrophilic groups against lipophilic groups). Patton, "Review of Fundamentals and Advances in Urethane Coating Technology," J. Paint Technology, 39:554–63 (1967), hereby incorporated by reference, describes applying the HLB rating system in the context of urethane systems. For purposes of this application, the HLB number of a polyol will be expressed as the total HLB number of the polyol divided by the number of hydroxy functional groups on the polyol.

A "polyisocyanate" is a molecule having two or more isocyanate groups available for reaction with hydroxyl groups to form urethane linkages.

A "polyol" is a molecule having two or more hydroxyl groups available for reaction with isocyanate groups to form urethane linkages.

A "prepolymer" is a partially polymerized polymer precursor that undergoes further reaction, with a corresponding increase in molecular weight, to form a final polymer.

A "water-curable" prepolymer is a prepolymer that cures (i.e., crosslinks) with or without a catalyst upon exposure to moisture vapor and/or liquid water.

A "coatable" prepolymer is a prepolymer having a viscosity that allows the prepolymer to be applied to the porous fabric at room temperature in the form of a substantially smooth, uniform coating.

A "microfiber filler" is a filler which, when incorporated into orthopedic casting materials according to the invention, provides an increase in strength without adversely affecting the viscosity of the uncured resin suspension (and thus the drapability of the casting material). Such fillers typically have an aspect ratio of at least five. For fibers having an irregular or non-circular cross section, the diameter of the fiber for the purposes of determining the aspect ratio is equal to the largest width across the microfiber.

"Warm wet strength" refers to the force required to crush a six layer ring tested according to the procedure described infra.

DETAILED DESCRIPTION

The invention features orthopedic casting materials in which the curable resin is a water-curable, isocyanate-functional prepolymer that is the reaction product of a polyisocyanate and a hydrophobic polyol having an HLB number per hydroxy group less than zero (preferably less than −3, more preferably less than −5). The polyol is preferably chosen to yield a prepolymer that is coatable in order to facilitate application of the prepolymer to a porous fabric sheet used in certain applications. In general, coatable prepolymers preferably have a viscosity between about 5 Pa s and about 500 Pa s (more preferably from about 10 Pa s to about 100 Pa s) when measured at 23° C. using a Brookfield RVT Rotovisco viscometer with a number 6 or 7 spindle and an operating speed of 10.

Suitable hydrophobic polyols include hydroxylated fatty acids (and esters thereof) such as glyceryl polyhydroxyoleates, e.g., glyceryl trihydroxyoleate. Glyceryl trihydroxyoleate contains three hydroxyoleic acid "branches," each having the following structure:

—OOC(CH$_2$)$_7$CH=CHCH$_2$COH(CH$_2$)$_5$CH$_3$

This structure has an HLB number of approximately −5 determined as described in Patton, supra. Specifically, each functional group is assigned an HLB number as follows:

| | |
|---|---|
| Ester (—COO—) | 1.1 |
| Ether (—O—) | 1.3 |
| Hydroxyl (—OH) | 1.9 |
| —CH$_3$ | −0.47 |
| —CH$_2$— | −0.47 |
| —CH— | −0.47 |

Accordingly, the HLB number for the structure:

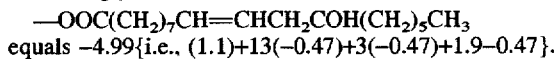
—OOC(CH$_2$)$_7$CH=CHCH$_2$COH(CH$_2$)$_5$CH$_3$ equals −4.99{i.e., (1.1)+13(−0.47)+3(−0.47)+1.9−0.47}.

In contrast, a polyoxyethylene chain having the structure —O—(CH$_2$CH$_2$O)$_8$—CH$_2$CH$_2$OH and a polyoxypropylene chain having the structure —O—(CH$_2$CH(CH$_3$)O)$_5$—CH$_2$CH(CH$_3$)OH, which form the basis of two polyether-based glycols typically used for orthopedic casting resins based upon polyisocyanate-terminated prepolymers, have HLB numbers per hydroxy group of approximately +5.14 and +1.24, respectively, owing to the presence of the hydrophilic ether linkages.

A particularly preferred polyol is castor oil, which is commercially available from Caschem Corp. of Bayonne, N.J. Castor oil is a triglyceride (ester) of a mixture of different fatty acids, with the predominant fatty acid by weight being 12-hydroxyoleic acid (otherwise known as ricinoleic acid, an 18-carbon acid having a double bond in the 9–10 position and a hydroxyl group on the 12th carbon). A typical Castor oil mixture is represented as follows (mole %):

Ricinoleic Acid 89.5%

Dihydroxystearic Acid 0.7%

Palmitic Acid 1.0%

Stearic Acid 1.0%

Oleic Acid 3.0%

Linoleic Acid 4.2%

Linolenic Acid 0.3%

Eicosanoic Acid 0.3%

Accordingly, the HLB number of castor oil is taken to be the weighted average of the HLB numbers of the different fatty acids (i.e., as attached to and including the glyceride chain) and is approximately −5.6(per hydroxy group).

Other suitable polyols include castor oil-based polyols commercially available from Caschem Corp. under the trade designation "CASPOL," including CASPOL 1842, CASPOL 1962, CASPOL 5001, CASPOL 5002, CASPOL 5003, CASPOL 5004, CASPOL 5005, CASPOL 5006, CASPOL 5007, CASPOL 5008, and DB Oil. The properties of these polyols are set forth below.

| Product | Equiv. wt. | Viscosity (cps) | Hydroxyl value | Specific gravity | Color (Gardner) | Functionality |
|---|---|---|---|---|---|---|
| CASPOL 1842 | 387 | 550 | 145 | 0.957 | 2 | 2 |
| CASPOL 1962 | 144 | 1400 | 390 | 0.966 | 3 | 3 |
| CASPOL 5001 | 193 | 300 | 290 | 0.960 | 3 | 2 |
| CASPOL 5002 | 164 | 850 | 342 | 0.985 | 3 | 3 |
| CASPOL 5003 | 214 | 430 | 262 | 0.965 | 3 | 2 |

-continued

| Product | Equiv. wt. | Viscosity (cps) | Hydroxyl value | Specific gravity | Color (Gardner) | Functionality |
|---|---|---|---|---|---|---|
| CASPOL 5004 | 173 | 3400 | 325 | 0.999 | 8 | 4 |
| CASPOL 5005 | 195 | 1400 | 288 | 1.020 | 2 | 5 |
| CASPOL 5006 | 200 | 1400 | 280 | 0.988 | 4 | 3.5 |
| CASPOL 5007 | 221 | 351 | 254 | 0.967 | 4 | 2 |
| CASPOL 5008 | 413 | 26,000 | 136 | 1.025 | 9 | — |
| DB Oil | 342 | 720 | 164 | 0.959 | 1+ | 27 |

Suitable polyisocyanates include diphenylmethane diisocyanate (MDI), 2,4-toluene diisocyanate (TDI), 2,6-toluene diisocyanate, 4,4'-diphenylmethane diisocyanate, 2,2'-diphenylmethane diisocyanate, aromatic polyisocyanates derived from phosgenation of the condensation product of aniline and formaldehyde, and mixtures thereof. A particularly preferred polyisocyanate is known as "ISONATE" 2143L commercially available from the Dow Chemical Company, which is a mixture of di- and triisocyanates containing about 73% of MDI.

The reactivity of the prepolymer once it has been exposed to moisture can be controlled by the use of a proper catalyst. The reactivity must not be so great that: (1) a hard film quickly forms on the prepolymer surface preventing further penetration of moisture into the bulk of the prepolymer; or (2) the cast become rigid before the application and shaping are complete. Examples of suitable catalysts include dimorpholinodiethyl ether ("DMDEE") prepared as described in U.S. Pat. No. 4,433,680 (hereby incorporated by reference) and 4-[2-[1-methyl-2-(4-morpholinyl)ethoxy]ethyl]-morpholine ("MEMPE") prepared as described in U.S. Pat. No. 4,705,840 (hereby incorporated by reference). Also suitable are amino-ester catalysts of the type described in U.S. Pat. No. 5,244,997 (hereby incorporated by reference). The catalysts are generally added at a concentration of about 0.05 to about 5 percent by weight (based on total prepolymer weight).

Foaming of the prepolymer is preferably minimized because it may adversely impact the surface smoothness of the cast and may decrease the cast's overall strength. Foaming may occur, for example, when carbon dioxide is released as a result of moisture reacting with an isocyanate group. One way to minimize foaming is to reduce the concentration of isocyanate groups in the prepolymer. Preferably, however, foaming is minimized by adding a foam suppressor such as silicone Antifoam A (commercially available from Dow Corning) or Anti-foam 1400 silicone fluid (commercially available from Dow Corning) to the reaction mixture. It is especially preferred to use a silicone liquid such as Dow Corning Anti-foam 1400 at a concentration of about 0.05 to 1.0 percent by weight. Water-curable resins containing a stable dispersion of hydrophobic polymeric particles, e.g., as disclosed in published European Patent Application No. EPO 0 407 056, may also be used to reduce foaming, as can antifoaming compositions sorbed on or encapsulated by a solid support, as described in U.S. Pat. No. 5,206,064 (hereby incorporated by reference).

Lubricants may be added to the reaction mixture in accordance with U.S. Pat. No. 4,667,661 (hereby incorporated by reference) such that the prepolymers exhibit reduced tack prior to and during cure, yet still form a cast with acceptable dry strength and lamination strength (as measured according to the test procedures described infra). Suitable lubricants are described in pending U.S. application Ser. No. 08/320,917 entitled "Novel Casting Material" filed Oct. 11, 1994 and assigned to the same assignee as the present application, which is hereby incorporated by reference, and include those having hydrophilic groups that covalently bond to the prepolymer, additives that are incompatible with the prepolymer (e.g., surfactants, polymers having a plurality of hydrophilic groups, and polysiloxanes), and combinations thereof. The lubricant may be used in conjunction with a separate fugitive liner if desired.

The prepolymer may further include one or more fillers if desired to provide increased dry strength and lamination strength. The fillers are added in an amount sufficient to provide the desired increase in strength without increasing the viscosity of the uncured prepolymer to the point where it is no longer coatable onto a fabric sheet or (in the case of casting materials lacking a fabric sheet) moldable by hand to conform to an injured body part. Examples of suitable fillers include microfiber fillers having an aspect ratio of, e.g., at least 5:1, as described in U.S. Pat. No. 5,354,259 (hereby incorporated by reference). Also suitable are spheres, bubbles, expandable bubbles, particulate materials, flakes and platelettype materials, and combinations thereof, as described in the aforementioned pending U.S. application Ser. No. 08/320,917.

In one embodiment, the resin is coated onto a porous fabric sheet such that the sheet is partially impregnated with the resin. Suitable sheets include nonwoven, woven, or knit fabrics made of natural or synthetic fibers or materials. To enhance inter-layer lamination, one or more of the sheets may be provided with a plurality of projections along at least one surface of the sheet, as described in U.S. Pat. No. 5,273,802 (hereby incorporated by reference). Preferably, each projection represents a bundle of at least about 8 filaments, and the sheet features about 75 to about 1500 projections (more preferably, about 1 to about 50 projections) per gram of fabric.

A particularly preferred sheet material is fiberglass, although non-fiberglass materials may be used as well. Examples of suitable non-fiberglass materials include fabrics made from natural organic fibers, animal-derived materials, naturally based organic polymer fibers, and synthetic polymer fibers. Examples of suitable natural organic fibers include vegetable-derived materials such as abaca, cotton, flax, hemp, jute, kapok, linen, ramie, and sisal, with cotton being preferred. Suitable animal-derived materials include wool, mohair, vicuna, other animal hairs, and silk, with wool being preferred.

Examples of suitable naturally based organic polymers include acetate, azlon, rayon, and triacetate. Suitable synthetically prepared organic polymers include acrylic, aramid, olefin (e.g., poly(1-butene), polyethylene, poly(3-methyl-1-butene), poly(1-pentene), polypropylene, poly(3-methyl-1-butene), poly(1-pentene), and polypropylene), polystyrene, polyester, polytetrafluoroethylene, poly(vinyl alcohol), poly(vinyl chloride), and poly(vinylidene chloride), with acrylic, nylon, polyethylene, polypropylene, polyester, and rayon being preferred. Examples of suitable knitted, woven, and/or non-woven sheets based upon these organic fibers are described, e.g., in U.S. Pat. Nos. 4,940,047; 4,984,566; and 4,841,958 (all of which are hereby incorporated by reference).

When fiberglass sheets are desired, suitable sheets which may be employed include knit fiberglass fabrics such as disclosed in U.S. Pat. Nos. 4,502,479; 4,609,578; 4,668,563; 5,014,403; and 5,353,486 (all of which are hereby incorporated by reference). Particularly preferred fiberglass sheets are extensible, heat-set, fiberglass fabrics as disclosed in U.S. Pat. No. 4,609,578.

In one preferred embodiment, the porous fabric is a light-weight scrim and the prepolymer is further provided with one or more fillers such that the total volume of fillers divided by the total volume of resin is greater than about 0.4, as described in pending U.S. application Ser. No. 08/320, 917. Such casting materials tend to exhibit a smoothness similar to that of plaster of Paris during cast application (making them easy to handle and apply), but exhibit sufficient post-cure strength for use as an orthopedic cast. The light-weight scrim (as described in the aforementioned U.S. patent application) typically accounts for less than 30% (and more preferably less than 20%) of the total weight of the uncured casting material. Suitable materials for the scrim include knits, wovens, non-wovens, and extruded porous sheets. Specific examples include cheesecloth, polypropylene (e.g., spunbonded polypropylene commercially available from AMOCO Fabrics and Fibers Co. of Atlanta, Ga. under the designation RFX™ nonwoven fabric), polyester, polyethylene, and polyamide. A light-weight scrim (6 grams/ $m^2$) comprising 1.75 denier, 3.8 cm long polyester staple fibers and coated at a basis weight of 2 grams/$m^2$ with Rhoplex B15 (from Rohm and Haas Co. of Philadelphia, Pa.) is particularly useful.

To further increase wet strength, a silane coupling agent may be applied to the porous fabric. Such agents covalently bond the resin to the porous fabric. One way to apply the coupling agent is to dip a bundle of the fabric into a solution of the coupling agent. However, to minimize the amount of coupling agent required, as well as the number of processing steps involved in application, it is preferred to apply the coupling agent to the surface of the fabric in a continuous process, as illustrated in FIGS. 1 and 2.

Referring to FIG. 1, a porous fiberglass fabric 10 passes over an idler roll 12 and into a silane application zone defined by opposed heads 20 and 22 of an atomizer or sprayer of conventional design for applying silane to both sides of fabric 10. Suitable spraying equipment includes sprayers with nozzle tips #800050 and 500017 from Spraying Systems Inc. The silane solution is pumped from a reservoir 24 through lines 26 and 28 to supply heads 22 and 20, respectively, of the atomizer/sprayer unit. Typically, the distance between the sprayer and the fabric will be between about 2 and 30 cm, more preferably between about 7 and 20 cm. The preferred distance may be determined by observing the spray pattern. The pump rate may be varied so as to apply the desired amount of silane onto the fabric. Typically, the amount of silane applied to the fabric, exclusive of any solvents used to apply the silane, is between about 0.1 and 2% by weight of the fabric, more preferably between about 0.1 and 1%.

Following silane application, the silane-coated fabric passes over a second idler roll 14 and into a drying oven 16. The temperature of the oven may be varied depending on the expected residence time that the fabric is in the oven. For example, the oven may be operated at a relatively low temperature, e.g., 49° C. when relatively long residence times are employed. Alternatively, the oven may comprise a flame of burning gas (e.g., methane, propane, butane) and the fabric may be passed quickly through the flame to accomplish the drying. Intermediate times and temperatures may also be employed. When the drying operation has been completed, the fabric then passes into a coating zone 30 where prepolymer is applied to form casting material 32.

FIG. 2 describes a second embodiment for continuously applying silane to the surface of a porous fiberglass fabric.

Referring to FIG. 2, a porous fiberglass fabric 110 passes over an idler roll 112 and into a silane application zone defined by porous pipes 120 and 122 (e.g., sintered stainless steel or plastic pipes) and take-up rollers 111 and 113. Suitable porous pipes include 1.9 cm diameter porous pipe available from Pore Technologies, Inc. The silane solution is pumped from a reservoir 124 through lines 126 and 128 to supply pipes 122 and 120, respectively. The silane solution then diffuses through the pores of pipes 120 and 122, and onto both sides of fabric 110. For this and the previous process the silane may be provided as a solution having between about 0.25 to 99% silane in a volatile solvent (e.g., water or water/methanol).

Following silane application, the silane-coated fabric passes over a second idler roll 114 and into a drying oven 116. When the drying operation has been completed, the fabric then passes into a coating zone 130 where prepolymer is applied to form casting material 132.

In some preferred embodiments, the porous fabric may be eliminated altogether, as described in the aforementioned U.S. application Ser. No. 08/320,917. As described therein, the resin is combined with one or more fillers of the type and amount to provide a casting material having sufficient void volume such that prior to cure, the material is sufficiently strong to allow the material to be applied to an injured limb or body part, but subsequent to cure has sufficient porosity to allow transport of water vapor (thereby enhancing comfort).

Summarized below are tests which were used to determine the "delamination strength" as well as the "ring strength" (measured in 3 different ways: "dry strength", "wet strength", and "warm wet strength"). Hence, whenever the terms "delamination strength" or "ring strength" (including the terms "dry strength", "wet strength", and "warm wet strength") are used herein, it will be understood that these terms refer to the delamination test and strength tests set forth herein, and that the values given for "delamination strength" and "ring strength" were determined in accordance with the following tests.

DELAMINATION TEST

This test measured the force necessary to delaminate a cured cylindrical ring of a resin-coated material within the scope of the present invention.

Each cylindrical ring comprised 6 layers of the resin-coated material having an inner diameter of 5.08 cm. The width of the ring formed was the same as the width of the resin-coated material employed, namely 7.62 cm. (The final calculation of the delamination strength is given in terms of newtons per centimeter of tape width.)

Each cylindrical ring was formed by taking a roll of the resin-coated material from its storage pouch and immersing the roll completely in deionized water having a temperature of about 27° C. for about 30 seconds. The roll of resin-coated material was then removed from the water and the material was wrapped around a 5.08 cm mandrel covered with a thin stockinet (such as 3M Synthetic Stockinet MS02) to form 6 complete uniform layers using a controlled wrapping tension of about 45 grams per centimeter width of the material. A free tail of about 15.24 cm was kept and the balance of the roll was cut off. Each cylinder was completely wound within 30 seconds after its removal from the water.

After 15 to 20 minutes from the initial immersion in water, the cured cylinder was removed from the mandrel, and after 30 minutes from the initial immersion in water its delamination strength was determined.

This was done by placing the free tail of the cylindrical sample in the jaws of the testing machine, namely, an "INSTRON" Model 1122 machine, and by placing a spindle through the hollow core of the cylinder so that the cylinder was allowed to rotate freely about the axis of the spindle. The "INSTRON" machine was then activated to pull on the free tail of the sample at a speed of about 127 cm/min. The average force required to delaminate the wrapped layers over the first 33 centimeters of the cylinder was then recorded in terms of force per unit width of sample (newtons/cm). For each material, at least 5 samples were tested, and the average delamination force was then calculated and reported as the "delamination strength."

RING STRENGTH TESTS

In these tests, the "dry strength", "wet strength", and "warm wet strength", of certain cured cylindrical ring samples of the resin-coated materials of the present invention were determined. For each of these tests, cured cylindrical ring samples were formed as described hereinabove with respect to the delamination test so as to form 6-layered cylinders around a 5.08 cm mandrel, only all excess material was trimmed off to form these cylindrical rings, leaving no tails.

At a point 30 minutes following the initial immersion in water, each cylinder was removed from its respective mandrel and allowed to cure for 48–60 hours in a controlled atmosphere of 23° C. ±2° C. and 50% ±5% relative humidity. Each cylinder was then placed in a fixture in a commercial testing instrument, e.g., an "INSTRON" instrument, and compression loads were applied to the cylindrical ring sample along its exterior and parallel to its axis. The cylindrical ring was placed lengthwise between the two bottom bars of the fixture (the bars being 1.9 centimeters wide, 1.3 centimeters in height, and 15.2 centimeters long), with the bars spaced about 4 centimeters apart. The inside edges of the bars were machined to form a curved surface having a 0.31 cm radius. A third bar (0.63 cm wide, 2.5 cm high, and 15.2 cm long) was then centered over the top of the cylinder, also parallel to its axis. The bottom or contacting edge of the third bar was machined to form a curved surface having a 0.31 cm radius. The third bar was brought down to bear against and crush the cylinder at a speed of about 5 cm/min. The maximum or peak force which was applied while crushing the cylinder was then recorded as the ring strength, which in this particular instance is the "dry strength" (expressed in terms of force per unit length of the cylinder, i.e., newtons/cm). For each material, at least 5 samples were tested, and the average peak force applied was then calculated and reported as the "dry strength."

To measure the "wet strength", the same procedure was followed as for the "dry strength", except that after curing for 48–60 hours, the cylinder was then immersed in water at about 45° C. for about 30 minutes, and then allowed to dry under ambient conditions for about 15 minutes. The cylinder was then placed in the instrument and crushed as described hereinabove in order to determine the "wet strength" thereof To determine the "warm wet strength" of the cylinder, the procedure was following exactly as set forth for the "wet strength" measurement above, with the exception that the cylinder was placed in the fixture and crushed immediately after removal from the 45° C. water bath and was not allowed to dry at all.

The invention will now be described further by way of the following examples.

EXAMPLES

Example 1

Casting Tape Having Silanated Backing

A 7.62 cm "SCOTCHCAST" II desized glass backing material, prepared as described in U.S. Pat. No. 4,609,578 (Reed), was coated with a 0.5% aqueous solution of A-1120 silane (available from Union Carbide, Danbury, Conn.). The coating was accomplished by spraying the silane solution onto the glass backing using an air brush spray gun. The extended silane treated backing was then oven dried, using a Dispatch oven at 49° C., for approximately 24 hours. The silanated backing was coated with urethane prepolymers (prepared using the methods described in U.S. Pat. No. 4,667,661 and the ingredients shown below for Resin #1, #2 and #3) using standard coating equipment in a dry room.

TABLE 1a

| Resin #1 (NCO/OH = 3.75/1) | | |
|---|---|---|
| Component | Wt. % | Grams |
| Isonate 2143L[1] | 54.99 | 1979.54 |
| Benzoyl Chloride | 0.05 | 1.80 |
| DB-100[2] | 0.20 | 7.27 |
| Butylated Hydroxytoluene | 0.07 | 17.28 |
| MEMPE[3] | 1.32 | 47.52 |
| Pluronic F108[4] | 4.00 | 144.00 |
| PPG-425[5] | 10.74 | 386.79 |
| PPG-725[6] | 28.22 | 1015.80 |

[1] Available from Dow Chemical Co.
[2] Available from Dow Chemical Co. under the tradename "Antifoam 1400".
[3] "MEMPE" = Morpholinoethylmorpholinoisopropyl ether
[4] Available from BASF
[5] A polypropylene glycol available from Arco Chemical Co. (Chicago, IL)
[6] A polypropylene glycol available from Arco Chemical Co. (Chicago, IL)

TABLE 1b

| Resin #2 (NCO/OH = 3.75/1) | | |
|---|---|---|
| Component | Wt. % | Grams |
| Isonate 2143L | 58.78 | 1881.08 |
| Castor Oil[1] | 33.48 | 1071.40 |
| MEMPE | 1.15 | 36.8 |
| Benzoyl Chloride | 0.06 | 1.88 |
| Butylated hydroxytoluene | 0.33 | 10.56 |
| Pluronic F108 | 5.00 | 160.00 |
| DB-100 antifoam | 0.20 | 6.24 |
| Cab-O-Sil TS-720[2] | 1.00 | 32.00 |

[1] Available from Caschem Inc., Bayonne, NJ or Amber Inc., Tarrytown, NY
[2] Available from Chem Serv, Minneapolis, MN TABLE 1c

| Resin #3 (NCO/OH = 3.75/1) | | |
|---|---|---|
| Component | Wt. % | Grams |
| Isonate 2143L | 52.30 | 1673.62 |
| Castor Oil | 17.92 | 573.56 |
| MEMPE | 1.15 | 36.91 |
| Benzoyl Chloride | 0.06 | 1.99 |
| Butylated hydroxytoluene | 0.33 | 10.59 |
| Pluronic F108 | 4.00 | 128.00 |
| DB-100 | 0.20 | 6.40 |
| PPG-2025[1] | 10.10 | 323.12 |

TABLE 1c-continued

Resin #3 (NCO/OH = 3.75/1)

| Component | Wt. % | Grams |
|---|---|---|
| LG-650[2] | 2.96 | 94.68 |
| NYAD G Wollastokup 100/2 | 5.00 | 160.02 |

[1]A polypropylene glycol available from Arco Chemical Co. (Chicago, IL)
[2]A low equivalent weight triol available from Arco Chemical Co. (Chicago, IL)

The resins were coated to a target coating wt. of 43.5%, rolled into 3.66 m lengths and packaged in conventional foil casting tape pouches. Several days later, standard 6 layer rings were made from the resin coated tapes by wrapping the tape around a 5.08 cm mandrel, after water activation, and allowing the resin coated rings to cure. Approximately 24 hours later the cured rings were tested.

TABLE 1d

| Results: (in N/cm width) | Resin #1 | Resin #2 | Resin #3 |
|---|---|---|---|
| 24 Hr. Dry Strength | 115.7 | 129.2 | 150.1 |
| Wet Strength | 75.2 | 120.3 | 137.7 |
| Warm Wet Strength | 19.4 | 97.5 | 113.7 |

EXAMPLE 2

A 7.62 cm Scotchcast® II desized glass backing material, prepared as described in U.S. Pat. No. 4,609,578(Reed), was coated with a 0.5% aqueous solution of A-0700 silane (N-(2-aminoethyl)-3-aminopropyltrimethoxysilane; available from Huils America, Piscataway, N.J.). The coating was accomplished by spraying the silane solution onto the glass backing using an air brush spray gun. The extended silane treated backing was then oven dried, using a Dispatch oven at 49° C., for approximately 24 hours. The silanated backing was coated with urethane prepolymers (prepared using the methods described in U.S. Pat. No. 4,667,661 and the ingredients shown below for Resin #4 and #5) using standard coating equipment in a dry room to a target coating weight of 43.5%. The above resins were also coated on untreated fiberglass tape to a target coating wt. of 43.5%.

TABLE 2a

Resin #4 (NCO/OH = 3.75/1)

| Chemical | Wt. % |
|---|---|
| Isonate 2143L | 55.39 |
| Benzoyl Chloride | 0.05 |
| DB-100 | 0.18 |
| Ionol | 0.48 |
| MEMPE | 1.15 |
| Pluronic F-108 | 4.00 |
| PPG-425 | 10.45 |
| PPG-725 | 28.31 |

TABLE 2b

Resin #5 (NCO/OH = 3.75/1)

| Chemical | Wt. % |
|---|---|
| Isonate 2143L | 58.53 |
| Castor Oil | 33.23 |

TABLE 2b-continued

Resin #5 (NCO/OH = 3.75/1)

| Chemical | Wt. % |
|---|---|
| MEMPE | 1.15 |
| Benzoyl Chloride | 0.06 |
| Ionol | 0.33 |
| Pluronic F-108 | 5.50 |
| DB-100 | 0.20 |
| Cab-O-Sil TS-720 | 1.00 |

The coated tapes were rerolled into 3.66 m lengths and packaged in a sealed foil pouches. The coating, rerolling, pouching operation was done in a dry room using standard coating equipment. Several days later, standard 6 layer rings were made from the resin coated tapes by wrapping the tape around a 5.08 cm mandrel, after water activation, and allowing the resin coated rings to cure. Approximately 24 hours later the cured rings were tested.

TABLE 2c

| | Resin #4 | | Resin #5 | |
|---|---|---|---|---|
| Results (in N/cm width) | without silane treatment | with silane treatment | without silane treatment | with silane treatment |
| 24 Hr. Dry Strength | 112.1 | 142.8 | 91.2 | 124.2 |
| Wet Strength | 52.9 | 106.1 | 53.3 | 119.9 |
| Warm Wet Strength | 21.4 | 43.6 | 43.3 | 95.8 |

The physical properties of the casting tapes having a silane treated backing were significantly higher than the corresponding casting tapes without the silane treated backing. The warm wet strength of the samples having castor oil were significantly higher than the corresponding sample that did not contain castor oil.

EXAMPLE 3

The following prepolymers were made and coated on desized, 7.62 cm, Scotchcast® II fiberglass casting tape backing. The coating process used standard coating equipment and took place in a dry room.

TABLE 3a

Resin #6

| Component | Wt. % | Grams |
|---|---|---|
| Isonate 2143L | 56.59 | 1810.98 |
| Benzoyl Chloride | 0.06 | 1.92 |
| DB-100 | 0.20 | 6.40 |
| Butylated hydroxytoluene | 0.33 | 10.56 |
| Castor Oil | 35.17 | 1125.35 |
| MEMPE | 1.15 | 36.80 |
| Pluronic F108 | 5.50 | 176.00 |
| Cab-O-Sil TS-720 | 1.00 | 32.00 |

TABLE 3b

Resin #7

| Component | Wt. % | Grams |
|---|---|---|
| Isonate 2143L | 56.09 | 1794.92 |
| Benzoyl Chloride | 0.06 | 1.92 |

TABLE 3b-continued

| Resin #7 | | |
| --- | --- | --- |
| Component | Wt. % | Grams |
| DB-100 | 0.02 | 6.34 |
| Butylated hydroxytoluene | 0.33 | 10.56 |
| Castor Oil | 34.82 | 1114.26 |
| Pluronic F108 | 5.50 | 176.00 |
| DMDEE[1] | 2.00 | 64.00 |
| Cab-O-Sil TS-720 | 1.00 | 32.00 |

[1]"DMDEE" = dimorpholinodiethyl ether

TABLE 3c

| Resin #8 | | |
| --- | --- | --- |
| Component | Wt. % | Grams |
| Isonate 2143L | 55.78 | 1785.07 |
| Benzoyl Chloride | 0.06 | 1.92 |
| DB-100 | 0.20 | 6.31 |
| Butylated hydroxytoluene | 0.33 | 10.56 |
| Castor Oil | 34.63 | 1108.14 |
| Pluronic F108 | 5.50 | 176.00 |
| DMDEE | 2.50 | 80.08 |
| Cab-O-Sil TS-720 | 1.00 | 32.00 |

The above prepolymers were coated to a target coating weight of 43.5%. The coated tape was cut to a 4 yard length and wrapped around a plastic core. The 3.66 m rolls were put into foil pouches and sealed prior to taking them from the dry room.

Several days later, the coated glass tapes were wrapped around a 5.08 cm mandrel and formed into 6 layer rings for testing. The formed rings were allowed to cure for at least 24 hours.

TABLE 3d

| Results: (in N/cm width) | Resin #6 | Resin #7 | Resin #8 |
| --- | --- | --- | --- |
| 24 Hr. Dry Strength | 120.8 | 112.5 | 106.6 |
| Wet Strength | 82.6 | 83.1 | 79.8 |
| Warm Wet Strength | 62.5 | 61.0 | 55.3 |
| Delamination Strength | 8.1 | 9.6 | 8.1 |
| Actual Resin Coating Wt. | 42.68% | 42.87% | 42.65% |

What is claimed is:

1. An orthopedic casting material comprising a porous fabric provided with a water-curable, isocyanate-functional prepolymer comprising the reaction product of a polyisocyanate and a polyol having an HLB number per hydroxy group less than zero.

2. The orthopedic casting material of claim 1 wherein said prepolymer comprises a coatable prepolymer.

3. The orthopedic casting material of claim 1 wherein said polyol has an HLB number per hydroxy group less than −3.

4. The orthopedic casting material of claim 1 wherein said polyol has an HLB number per hydroxy group less than −5.

5. The orthopedic casting material of claim 1 wherein said polyol comprises a hydroxylated fatty acid or ester thereof.

6. The orthopedic casting material of claim 1 wherein said polyol comprises a glyceryl polyhydroxyoleate.

7. The orthopedic casting material of claim 1 wherein said polyol comprises a glyceryl trihydroxyoleate.

8. The orthopedic casting material of claim 1 wherein said polyol comprises castor oil.

9. The orthopedic casting material of claim 1 wherein said material has a warm wet strength of at least 35N/cm following cure.

10. The orthopedic casting material of claim 1 wherein said fabric comprises a knitted or woven fabric.

11. The orthopedic casting material of claim 1 wherein said fabric comprises fiberglass fabric.

12. The orthopedic casting material of claim 1 wherein said fabric comprises a knitted or woven fiberglass fabric having on at least one side thereof a plurality of projections, each said projection comprising a bundle of at least about 8 filaments, said side of said fabric having from about 75 to about 1500 projections per gram of fabric.

13. The orthopedic casting material of claim 1 wherein said fabric comprises a knitted or woven fiberglass fabric having on a least one side thereof a plurality of projections, each said projection comprising a bundle of at least 8 filaments, said side of said fabric having from about 1 to about 50 projections per square centimeter.

14. The orthopedic casting material of claim 1 wherein said fabric has a major surface provided with a lubricant, and wherein said material has a warm wet strength of at least 60N/cm following cure.

15. The orthopedic casting material of claim 1 wherein said fabric comprises a light-weight scrim and said casting material further comprises one or more fillers, the total volume of said fillers divided by the volume of said prepolymer being greater than about 0.4.

16. The orthopedic casting material of claim 1 wherein said fabric has a major surface provided with a silane coupling agent.

17. The orthopedic casting material of claim 16, wherein said material has a warm wet strength of at least 90N/cm following cure.

18. The orthopedic casting material of claim 1 further comprising one or more microfiber fillers having an aspect ratio of at least 5:1.

19. An orthopedic casting material comprising a porous fabric provided with a coatable, water-curable, isocyanate-functional prepolymer comprising the reaction product of a polyisocyanate and a polyol comprising castor oil.

20. An orthopedic casting material comprising:
one or more fillers; and
a water-curable, isocyanate-functional prepolymer comprising the reaction product of a polyisocyanate and a polyol having an HLB number per hydroxy group less than zero, wherein said orthopedic casting material has a sufficient tensile strength prior to cure to resist tensile stresses imparted during wrapping of a cast, and a sufficient void volume after cure to allow transport of water vapor.

21. The orthopedic casting material of claim 20 wherein said polyol has an HLB number per hydroxy group less than −5.

22. The orthopedic casting material of claim 20 wherein said polyol comprises a hydroxylated fatty acid or ester thereof.

23. The orthopedic casting material of claim 20 wherein said polyol comprises a glyceryl polyhydroxyoleate.

24. The orthopedic casting material of claim 20 wherein said polyol comprises castor oil.

25. An orthopedic casting material comprising:
one or more fillers; and a light-weight scrim provided with a water-curable, isocyanate-functional prepolymer comprising the reaction product of a polyisocyanate and a polyol having an HLB number per hydroxy group less than zero, wherein the total volume of said fillers divided by the volume of said prepolymer is greater than about 0.4.

26. The orthopedic casting material of claim 25, wherein said polyol comprises castor oil.

27. An orthopedic casting material comprising a porous fabric provided with a water-curable, isocyanate-functional prepolymer comprising the reaction product of a polyisocyanate and a polyol, wherein said orthopedic casting material has a warm wet strength of at least 40N/cm following cure.

28. The casting material of claim 27, wherein said polyol comprises castor oil.

* * * * *